United States Patent [19]

Chang et al.

[11] Patent Number: 4,511,724

[45] Date of Patent: Apr. 16, 1985

[54] 5-(PYRROL-2-OYL)-1,2-DIHYDRO-3H-PYRROLO [1,2-A]PYRROLE DERIVATIVES AS ANTI-INFLAMMATORY AND ANALGESIC AGENTS

[75] Inventors: Michael N. Chang; Tesfaye Biftu, both of Westfield, N.J.

[73] Assignee: Merck & Co., Inc., Rahway, N.J.

[21] Appl. No.: 449,302

[22] Filed: Dec. 13, 1982

Related U.S. Application Data

[63] Continuation-in-part of Ser. No. 387,079, Jun. 10, 1982, abandoned.

[51] Int. Cl.$^3$ .................. C07D 487/06; A61K 31/40
[52] U.S. Cl. .................... 548/452; 514/825; 547/173; 547/373; 546/200; 536/55.2
[58] Field of Search .................. 548/452; 544/173; 579/373; 546/200; 536/55.2

[56] References Cited

U.S. PATENT DOCUMENTS 4,097,579 6/1978 Muchowski et al. ............... 548/452
4,232,038 8/1979 Kluge et al. ....................... 548/452

FOREIGN PATENT DOCUMENTS 0032048 12/1980 European Pat. Off. .
41711 12/1981 European Pat. Off. .

OTHER PUBLICATIONS

Franco et al., J. O. Chem., vol. 47, (1982) pp. 1682–1688.

Primary Examiner—Glennon H. Hollrah
Assistant Examiner—D. B. Springer
Attorney, Agent, or Firm—Theresa Y. Cheng

[57] ABSTRACT

Substituted 5-(pyrrol-2-oyl)1,2-dihydropyrrolo[1,2-a]-pyrrole derivatives have been prepared via decarboxylation of the corresponding 1,7-dicarboxylate prepared from condensation of a dialkyl 1,2-dihydro-3H-pyrrolo[1,2-a]pyrrole-1-7-dicarboxylate-7-carboxylic acid with an appropriately substituted 2-pyrroyl chloride, or conversely, an acid chloride of the former bicyclic compounds with a substituted pyrrole. The compounds are analgesic and anti-inflammatory agents of high activities but low ulcerogenic side effects.

8 Claims, No Drawings

5-(PYRROL-2-OYL)-1,2-DIHYDRO-3H-PYRROLO[1,2-A]PYRROLE DERIVATIVES AS ANTI-INFLAMMATORY AND ANALGESIC AGENTS

RELATED APPLICATION

This application is a continuation-in-part of application Ser. No. 387,079, filed June 10, 1982, abandoned.

BACKGROUND OF THE INVENTION

The present invention relates to novel substituted 5-(pyrrol-2-oyl)-1,2-dihydro-3H-pyrrolo [1,2-a]pyrrole derivatives and their corresponding salts, esters, nitriles, amides and substituted amides. Unlike the known pyrrolo[1,2-a]pyrrole derivatives of U.S. Pat. No. 4,097,579, which are limited to 5-unsubstituted pyrryl derivatives, the new compounds of the present invention have 5-pyrryl groups substituted with various groups including alkyl, 5-S-alkyl,

5-$SO_2$-alkyl, 5-alkyl, 5-N-alkyl, 5-O-alkyl or 5-halo. It has been a well-known fact that such hetero-substituted pyrroles are difficult to prepare due to the sensitive nature of the pyrrole system. Furthermore, the compounds of this invention are found to possess higher analgesic/anti-inflammatory activities but exhibit much lower ulcerogenic irritation than the prior art compounds. For a chronic disease, for example, arthritis, it is crucial that the anti-inflammatory/analgesic agent be administered routinely and regularly at an effective dosage level without causing gastric irritation or ulcer. Accordingly, it is an object of the present invention (1) to provide novel nonsteroidal anti-inflammatory and analgesic agents with high potency but lower ulcerogenic side effect;

(2) to develop processes for the preparation of the novel 5-(substituted pyrrol-2-oyl)-1,2-dihydro-3H-pyrrolo[1,2-a]pyrrole derivatives;

(3) to provide methods of application of the novel compounds in the treatment of inflammatory diseases, the relief of pain and fever or inhibition of platelet aggregation; and (4) to provide pharmaceutical compositions and formulations for the administration of these novel compounds.

DETAILED DESCRIPTION OF THE INVENTION

This invention relates to novel 5-(substituted pyrrol-2-oyl)-1,2-dihydro-3H-pyrrolo[1,2-a]pyrrole derivatives of the structural formula:

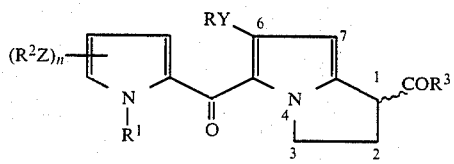

or a pharmaceutically acceptable salt, ester or amide thereof wherein

R is (a) hydrogen;

(b) loweralkyl especially $C_{1-6}$ linear or branched alkyl such as methyl, ethyl, propyl, isopropyl, t-butyl, pentyl, and hexyl;

(c) lowercycloalkyl especially $C_{3-6}$ cycloalkyl such as cyclopropyl, cyclobutyl, cyclopentyl and cyclohexyl;

(d) lower(cycloalkyl-alkyl) especially $C_{4-8}$ (cycloalkylalkyl) such as cyclopropylmethyl, cyclopentylmethyl, cyclohexylmethyl and cyclohexylethyl;

(e) loweralkenyl especially $C_{2-8}$ alkenyl such as 2-propenyl, 2-methyl-2-butenyl and 3-ethyl-2-pentenyl;

(f) halo-loweralkyl especially halo $C_{1-6}$ alkyl such as chloromethyl, trifluoromethyl, 1-chloroethyl and 2,2-difluorobutyl; or (g) phenyl- or substituted phenyl-loweralkyl especially phenyl-$C_{1-3}$ alkyl such as benzyl, 4-chlorobenzyl, 2-fluorobenzyl, and phenylpropyl.

groups (a)–(g) above being unsubstituted or substituted by loweralkyl, loweralkoxy, halo, cyano, carboxy, sulfonamino, carbamoyl, sulfonyl, sulfinyl, azido, amino, substituted amino such as loweralkylamino or diloweralkylamino, haloalkyl, carboxyalkyl, carbamoylalkyl, N-sustituted carbamoylalkyl or a combination thereof;

$R^1$ is hydrogen, haloloweralkyl or loweralkyl especially $C_{1-6}$ alkyl as previously defined;

$R^2Z$ can be at any available ring positions and $R^2$ is R as previously defined;

n is 1 to 3;

$R^3$ is (a) hydroxy;

(b) loweralkoxy especially $C_{1-6}$ alkoxy as defined previously;

(c) amino;

(d) loweralkylamino especially $C_{1-6}$ alkylamino such as cyclohexylamino, methylamino, isopropyl amino, n-butylamino or t-butylamino;

(e) diloweralkylamino especially di($C_{1-6}$ alkyl)amino such as diethylamino, or dimethylamino;

(f) morpholinyl;

(g) bis(hydroxyloweralkyl)amino especially bis(hydroxy $C_{1-6}$ alkyl)amino such as bis(hydroxyethyl)amino;

(h) loweralkylcyclohexylamino especially $C_{1-6}$ alkylcyclohexyamino such as methylcyclohexylamino; or (i) glucosamino;

(j) lower(alkanoyloxyalkoxy), especially $C_{1-6}$ (alkanoyloxyalkoxy) such as 1-(pivaloyloxy)ethoxy or 1-(acetoxy)ethoxy;

(k) aroyloxylweralkoxy especially 1-(benzoxy)ethoxy;

(l) lower(alkoxycarbonyloxyalkoxy) especially $C_{1-6}$ (alkoxycarbonyloxyalkoxy) such as 1-(ethoxycarbonyloxy)ethoxy;

(m) aryloxycarbonyloxyloweralkoxy especially aryloxycarbonyl $C_{1-6}$ alkoxy such as 1-(benzyloxycarbonyloxy)ethoxy;

(n) tri(loweralkylamino)loweralkoxy especially tri ($C_{1-6}$ alkoxy such as choline-oxy;

(o) lower(alkanoylaminoalkoxy), especially $C_{1-6}$ (alkanoylaminoalkoxy) such as acetamidoethoxy;

(p) imidoloweralkoxy especially imido $C_{1-6}$ alkoxy such as 1-(succinimido)ethoxy;

(q) heterocyclyloxy, for example, phthalidyloxy, or 2-pyridyloxy;

(r) hydroxyloweralkoxy especially hydroxy $C_{1-6}$ alkoxy such as hydroxypropoxy;

(s) loweralkoxyalkoxy especially $C_{1-6}$ (alkoxyalkoxy) such as methoxyethoxy, ethoxyethoxy or methoxymethoxy;

(t) di(loweralkylamino)loweralkoxy especially di($C_{1-6}$ alkylamino) $C_{1-6}$ alkoxy such as dimethylamino ethoxy, dimethylamino-propoxy, or diethylamino propoxy;

(u) N-pyrrolidinylloweralkoxy especially N-pyrrolidinyl $C_{1-6}$ alkoxy such as N-pyrrolidinylethoxy or N-pyrrolidinyl methoxy and N-methyl-2-pyrrolidinyl-methoxy;

(v) N-piperidinylloweralkoxy especially N-piperidinyl $C_{1-6}$ alkoxy such as N-piperidinylethoxy;

(w) N-morpholinylloweralkoxy especially N-morpholinyl $C_{1-6}$ alkoxy such as N-morpholinylethoxy; or (x) 4-methyl-1-piperazinylloweralkoxy especially 4-methyl-1-piperazinyl $C_{1-6}$ alkoxy such as 4-methyl-1-piperazinylethoxy;

Y is oxygen, sulfur, sulfinyl, sulfonyl, $CH_2$— or hydrogen providing that when Y is hydrogen, R does not exist; and Z is —O—, —S—, —SO—, —$SO_2$—, —NH—, —$CH_2$ or halo especially fluoro, chloro or bromo providing that when Z is halo, $R^2$ does not exist.

The preferred embodiment of this invention comprises compounds of formula (I) wherein R is (a) hydrogen or $C_{1-6}$ alkyl as previously defined;

(b) $C_{2-4}$ alkenyl such as 2-propenyl or propenylmethyl;

(c) halo-$C_{1-6}$ alkyl as previously defined; or (d) phenyl-$C_{1-3}$ alkyl such as benzyl;

$R^1$ is hydrogen or $C_{1-6}$ alkyl;

$R^2Z$ is at position 5, i.e. adjacent to N and is R as defined above;

n is 1;

$R^3$ is hydroxy, $C_{1-6}$ alkoxy, or lower(alkanoylaminoalkoxy), especially $C_{1-6}$ alkanoylaminoalkoxy such as acetamidoethoxy;

Y is oxygen, sulfur, $CH_2$-, or H when R is absent; and

Z is —S—, —$CH_2$—, or halo when $R^2$ is absent.

The most preferred embodiment of this invention comprises compounds of structural formula (I) wherein $R_1$ is $C_{1-3}$ alkyl especially methyl or absent;

$R^1$ is hydrogen or methyl;

$R^2Z$ is at position 5 and $R^2$ is hydrogen, methyl, or absent;

n is 1;

$R^3$ is hydroxy, $C_{1-6}$ alkoxy or acetamidoethoxy;

Y is oxygen, $CH_2$—, or H with the proviso that when Y is H, R is absent; and

Z is —S—, —$CH_2$—, or halo with the proviso that when Z is halo, $R^2$ is absent.

The representative compounds of this invention comprise:

(1) 5-(5-methylthio-2-pyrroyl)-1,2-dihydro-6-methyl-3H-pyrrolo[1,2-a]pyrrole-1-carboxylic acid;

(2) ethyl 5-(5-methylthio-2-pyrroyl)-1,2-dihydro-6-methyl-3H-pyrrolo[1,2-a]pyrrole-1-carboxylate;

(3) 5-(5-chloro-2-pyrroyl)-1,2-dihydro-6-methyl-3H-pyrrolo[1,2-a]pyrrole-1-carboxylic acid; or (4) ethyl 5-(5-chloro-2-pyrroyl)-1,2-dihydro-6-methyl-3H-pyrrolo[1,2-a]pyrrole-1-carboxylate;

(5) 5-(5-isopropyl-2-pyrroyl)-1,2-dihydro-6-methyl-3H-pyrrolo[1,2-a]pyrrole-1-carboxylic acid;

(6) ethyl 5-(5-isopropyl-2-pyrroyl)-1,2-dihydro-6-methyl-3H-pyrrolo[1,2-a]pyrrole-1-carboxylate; or (7) 5-(1-methyl-5-methylthio-2-pyrroyl)-1,2-dihydro-6-methyl-3H-pyrrolo[1,2-a]pyrrole-1-carboxylic acid;

(8) ethyl 5-(1-methyl-5-methylthio-2-pyrroyl-1,2-dihydro-6-methyl-3H-pyrrolo[1,2-a]pyrrole-1-carboxylate;

(9) 5-(1-methyl-5-chloro-2-pyrroyl)-1,2-dihydro-6-methyl-3H-pyrrolo[1,2-a]pyrrole-1-carboxylic acid;

(10) ethyl 5-(1-methyl-5-chloro-2-pyrroyl)-1,2-dihydro-6-methyl-3H-pyrrolo[1,2-a]pyrrole-1-carboxylate;

(11) 5-(1-methyl-5-isopropyl-2-pyrroyl)-1,2-dihydro-6-methyl-3H-pyrrolo[1,2-a]pyrrole-1-carboxylic acid;

(12) ethyl 5-(1-methyl-5-isopropyl-2-pyrroyl)-1,2-dihydro-6-methyl-3H-pyrrolo[1,2-a]pyrrole-1-carboxylate;

(13) 5-(1-methyl-5-ethylthio-2-pyrroyl)-1,2-dihydro-6-methyl-3H-pyrrolo[1,2-a]pyrrole-1-carboxylic acid;

(14) 5-(1-methyl-5-n-propylthio-2-pyrroyl)-1,2-dihydro-6-methyl-3H-pyrrolo[1,2-a]pyrrole-1-carboxylic acid;

(15) 5-(1-methyl-5-methoxy-2-pyrroyl)-1,2-dihydro-6-methyl-3H-pyrrolo[1,2-a]pyrrole-1-carboxylic acid;

(16) 5-(1-methyl-5-ethoxy-2-pyrroyl)-1,2-dihydro-6-methyl-3H-pyrrolo[1,2-a]pyrrole-1-carboxylic acid;

(17) 5-(1-methyl-5-n-propyloxy-2-pyrroyl)-1,2-dihydro-6-methyl-3H-pyrrolo[1,2-a]pyrrole-1-carboxylic acid;

(18) 5-(1-trifluoromethyl-5-methylthio-2-pyrroyl)-1,2-dihydro-6-methyl-3H-pyrrolo[1,2-a]pyrrole-1-carboxylic acid;

(19) ethyl-5-(1-methyl-5-ethylthio-2-pyrroyl)-1,2-dihydro-6-methyl-3H-pyrrolo[1,2-a]pyrrole-1-carboxylate;

(20) ethyl 5-(1-methyl-5-n-propylthio-2-pyrroyl)-1,2-dihydro-6-methyl-3H-pyrrolo[1,2-a]pyrrole-1-carboxylate;

(21) ethyl 5-(1-methyl-5-methoxy-2-pyrroyl)-1,2-dihydro-6-methyl-3H-pyrrolo[1,2-a]pyrrole-1-carboxylate;

(22) ethyl 5-(1-methyl-5-ethoxy-2-pyrroyl)-1,2-dihydro-6-methyl-3H-pyrrolo[1,2-a]pyrrole-1-carboxylate;

(23) ethyl 5-(1-methyl-5-n-propyloxy-2-pyrroyl)-1,2-dihydro-6-methyl-3H-pyrrolo[1,2-a]pyrrole-1-carboxylate;

(24) ethyl 5-(1-trifluoromethyl-5-methylthio-2-pyrroyl)-1,2-dihydro-6-methyl-3H-pyrrolo[1,2-a]pyrrole-1-carboxylate; or a sodium or lysine salt of the carboxylic acids described above.

It is intended that compounds of the present invention include their corresponding optical isomers (d-, l-, or dl-form) especially the l-isomers. The asymmetric center of the compound is as shown below at carbon number one:

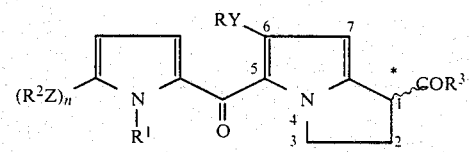

The novel compounds of the present invention can be prepared by the precursor IIa as shown in the following scheme:

(IIa diagram showing pyrrole structure with RY, COOR⁵, COOR⁴, (R²Z)ₙ, N-R¹, O substituents)

↓

(Ia diagram showing pyrrole structure with RY, COOR⁴, (R²Z)ₙ, N-R¹, O substituents)

↓ Appropriate modifications (I)

wherein R, Y, R¹, R², Y and Z are as previously defined and R⁴ is hydrogen, loweralkyl especially $C_{1-6}$ alkyl such as methyl, ethyl, isopropyl, t-butyl, pentyl, or cyclohexyl, and R⁵ is hydrogen, t-butyl, benzhydryl or other acid-removable protecting groups which can be removed under mild conditions.

According to the scheme above, IIa is decarboxylated under neutral, acidic or basic conditions or by itself (neat). When the decarboxylation is conducted under basic conditions, the precursor of formula IIa is usually heated with a base (Table II) in an appropriate solvent at about 50°–250° C. preferably about 90°–150° C. for about 0.5–48 hours or until the decarboxylation is substantially complete.

The most commonly utilized solvents comprise
(1) water;
(2) $C_{1-5}$ alkanol especially methanol, ethanol, isopropanol and t-butyl alcohol;
(3) lower ketone, e.g., acetone and methylethylketone;
(4) lower ether including 1,2-dimethoxyethane, tetrahydrofuran (THF), dioxane and diglyme;
(5) a mixture of at least two of the solvents described in (1) to (4) especially aqueous solutions thereof.

TABLE I

Organic Bases Used in Decarboxylation

Tri-(loweralkyl)amine, e.g.,
  triethylamine
  pyrrolidine
  pyridine
  collidine When acidic decarboxylation is applied, for example, IIa is refluxed in trifluoroacetic acid to give Ia which is then subject to various known modifications such as hydrolysis (when R⁴ is not H), ammonialysis, ester exchange etc. to afford (I). Other acids may also be used. For example, those listed below in Table II.

TABLE II

Acids Used in the Decarboxylation (1) An acid of the structural formula:

$$R^7-\underset{\underset{R^8}{|}}{\overset{\overset{R^6}{|}}{C}}-COOH$$

wherein R⁶ and R⁸ independently are hydrogen or halo such as iodo, bromo, chloro or fluoro preferably chloro or fluoro; and R⁷ is H, $C_{1-6}$ alkyl, halo especially chloro or fluoro, or halo-$C_{1-6}$ alkyl such as trifluoromethyl, trichloromethyl, 1,1-difluoroethyl, or 1-chloro-1-fluoropropyl or the like.

(2) Preferred Acids:
  Acetic acid
  Chloroacetic acid
  Chlorodifluoroacetic acid
  Dichloroacetic acid
  Difluoroacetic acid
  Trifluoroacetic acid
  Trichloroacetic acid
  Pentafluoropropanoic acid The acidic decarboxylation may be conducted in an acid or in an inert solvent containing the acid. The solvents which are often used are illustrated below in Table III.

TABLE III

Solvents for the Acidic Decarboxylation

Toluene
Benzene
Xylene
Tetrahydrofuran
1,2-Dimethoxy-ethane
Dioxane
Methylene chloride
Acetic Acid The decarboxylation temperatures may vary with the acids or solvents being used. Usually the temperatures range from about 30° to about 120° C. Under the optimum conditions, i.e., in refluxing trifluoroacetic acid with or without solvent, the temperature ranges from about 35° to about 75° C.

Generally, the decarboxylation is substantially complete after heating at an appropriate temperature for about 1 to about 20 hours or under more favorable conditions, about 0.5 hours to about 5 hours.

The prescursors of formula IIa are readily prepared from condensation between a pyrrolo[1,2-a]-pyrrole moiety and a substituted pyrrole derivative as shown below in scheme (a):

Scheme (a)

(IIIa diagram showing pyrrole with RY, COOR⁵, COOR⁴ substituents) $\xrightarrow{COCl_2}$ -continued
Scheme (a)

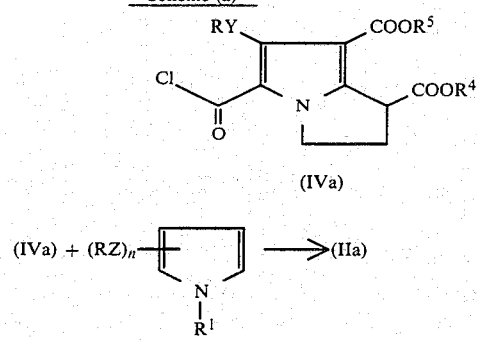

(IVa)

(IVa) + (RZ)$_n$ ⟶ [pyrrole with N-R¹] ⟶ (IIa)

wherein R, R¹, R², R⁴, R⁵, Y and Z are as previously defined.

Alternatively where Z is —S—, —O—, or —NH—, IIa may be obtained via the following scheme (b):

Scheme (b)

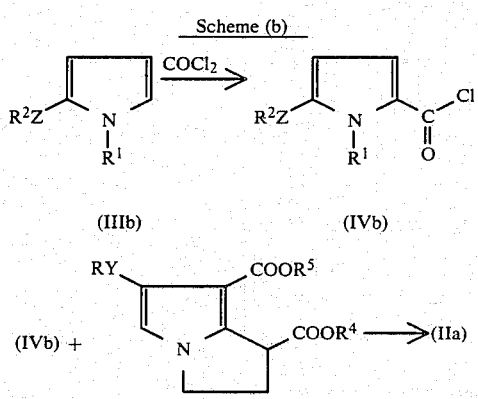

(IVb) + [pyrrole] ⟶ (IIa)

The starting materials (IIIa and IIIb) are known or readily preparable by procedures described in copending application Ser. No. 373,692, filed May 31, 1982 (our Case 16617IA) and U.S. Pat. No. 4,097,579. These two disclosures are herein incorporated by reference.

The pharmaceutically acceptable salts of the acids of the Formula I are readily prepared by conventional procedures well-known in the art. For example, an acid of Formula I is treated with an appropriate amount of a base, such as an alkali or alkaline earth metal hydroxide, e.g. sodium hydroxide, potassium hydroxide, calcium hydroxide, or an organic base such as an amine, e.g., triethylamine, lysine, dibenzylethylenediamine, piperidine, pyrrolidine, benzylamine and the like.

The pharmaceutically acceptable esters of the acids of structural formula (I) are prepared by conventional methods. For example, (1) A compound of Formula (I) is treated with a lower alkanol or phenol in the presence of an acid such as sulfuric acid, hydrochloric acid and any one or a combination of the acids illustrated above in Table (II) or ion exchange resins.

(2) A compound of Formula (I) is converted to an acid halide such as acid chloride or bromide via treatment with a halogenating agent such as thionyl chloride or phosphorus pentachloride, followed by reaction with an alcohol or a phenol. Other well-known methods such as those included in the "Compendium of Organic Synthetic Methods," I. T. Harrison et al., Wiley-Interscience, p. 272 (1971), may also be used.

Similarly, the pharmaceutically acceptable amides of the acids of Formula (I) are readily prepared by conventional methods. For example, the halides of the acids of Formula (I) can be treated with ammonia or substituted amines such as ethylamine, benzylamine or glucosamine to afford the corresponding amides. Other methods involving treatment of the acids with an amine in the presence of a catalyst such as DDC or tosylchloride may also be used.

The following examples are provided for illustrating but not limiting, the scope of the present invention.

EXAMPLE 1

Step A: Preparation of 1-Methyl-2-thiocyanopyrrole

Under nitrogen atmosphere, to a mixture of 25 g of KSCN in 60 ml of dry methanol at −78° C. was added 20 g of Br$_2$ dissolved in 45 ml of methanol. The resulting yellow solution was stirred for 5–10 minutes and 10.1 g of 1-methylpyrrole added in one portion. The mixture was allowed to warm to room temperature and stirred for an additional hour. The mixture was poured into 600 ml of ice-water and extracted twice with 200 ml of methylene chloride. The methylene chloride layer was washed, dried and then concentrated to yield 16.1 g of light yellow oil that turns reddish upon standing.

Step B: Preparation of 1-methyl-2-methylthiopyrrole

Under nitrogen atmosphere, to a mixture of 6.9 g of 1-methyl-2-thiocyanopyrrole and 14.2 g of CH$_3$I at −30° C., 5.4 g of sodium methoxide was added an the temperature allowed to rise to 0° C. The reaction mixture boiled (exothermic reaction). Stirring was continued for 3 hours at ambient temperature. The filtrate was desolventized under reduced pressure to yield 5.75 g of light yellow oil. This product (clean by NMR) could be distilled at T 40° C. under vacuum and stored over K$_2$CO$_3$ at 0° C.

Step C: Preparation of 1-methyl-5-methylthiopyrrole-2-acid chloride

To a solution of 12.7 g of 1-methyl-2-methylthiopyrrole in 100 ml of dry ether stirred over an atmosphere of nitrogen at 0° C., 11 g of phosgene dissolved in 20 ml of ether was added. This mixture was stirred at 0° C. for 4 hours and ambient temperature for 14 hours. Residual phosgene was removed with N$_2$ and solvent distilled off. The resulting solid product was recrystallized from hexane to yield 17 g of pink long needles, m.p. 67°–70° C.

Step D: Preparation of Ethyl 1-(2-hydroxyethyl)-3-carboethoxy-4-methylpyrrole-2-acetate To a solution of 1500 ml of ethanolamine in 1250 ml of water at −20° C., 505 g of diethyl-1,3-acetonedicarboxylate was added and the mixture stirred for 125 minutes at 0° C. and then treated with 237 g of 1-chloroacetone. The reaction temperature was maintained below 10° C. After additional stirring at room temperature for 5 hours, the mixture was poured to 2 1 HCl-6 Kg ice and stirred for about ½ hour. The mixture was filtered and the residue washed thoroughly with H$_2$O, and then hexane to yield 200 g of white product. m.p. 133°–135° C.

Step E: Preparation of Ethyl 1-(2-mesyloxyethyl)-3-carboethoxy-4-methylpyrrole-2-acetate Ethyl 1-(2-hydroxyethyl)-3-carboethoxy-4-methylpyrrole-2-acetate (101.7 g) in 800 ml of dry methylene chloride at −10° C. was treated with 56 ml of triethylamine followed by addition dropwise 31 ml of methanesulfonyl chloride. After 30 minutes of stirring at room temperature, 250 ml of water was added and the organic layer separated and washed with water (3×300 ml), dried over Na$_2$SO$_4$ and evaporated under reduced pressure to yield 121.3 g of ethyl 1-(2-mesyloxyethyl)-3-carboethoxy-4-methyl-pyrrole-2-acetate as white crystals from ethylacetate hexane, m.p. 66°–68° C.

Step F: Preparation of Ethyl 1-(2-iodoethyl)-3-carboethoxy-4-methylpyrrole-2-acetate Ethyl 1-(2-mesyloxyethyl)-3-carboethoxy-4-methyl-pyrrole-2-acetate (11.6 g) and 27 g of NaI was heated to reflux with 150 ml of acetonitrile for 1 hour. Solvent was removed by distillation and the residue triturated with water. The insoluble product was separated by filtration, air dried and crystallized from methylenechloride/hexane to yield 14.9 g of ethyl 1-(2-iodoethyl)-3-carboethoxy-4-methylpyrrole-2-acetate as a white solid.

Step G: Preparation of Diethyl 1,2-dihydro-6-methyl-3H-pyrrolo-[1,2-a]pyrrole-1,7-dicarboxylate Ethyl 1-(2-iodoethyl)-3-carboethoxy-4-methyl-pyrrole-2-acetate in 65 ml of dry dimethylformamide was treated with 1.6 g NaH (60% in mineral oil) and stirred for 60 minutes at room temperature. The mixture was quenched with 100 ml of water and extracted with ethylacetate (3×100 ml). The ethyl acetate layer was washed with water, dried over MgSO$_4$, filtered and evaporated to dryness to yield 6.4 g of crude diethyl 1,2-dihydro-6-methyl-3H-pyrrolo-[1,2-a]pyrrole-1,7-dicarboxylate to be used in the next step without further purification.

Step H: Preparation of Diethyl 5-(1-methyl-5-methylthio-2-pyrroyl)-1,2-dihydro-6-methyl-3H-pyrrolo-[1,2-a]pyrrole-1,7-dicarboxylate Diethyl 1,2-dihydro-3H-pyrrolo-[1,2-a]-6-methylpyrrole-1,7-dicarboxylate (22.2 g) and 16 g of 1-methyl-5-methylthiopyrrole-2-acid chloride were dissolved in 250 ml of methylene chloride at 0° C. followed by dropwise treatment with 22 ml of SnCl$_4$ in 45 ml of methylene chloride. After additional stirring at ambient temperature for 3 hours, 250 ml 3N HCl was added and then stirred for 1 hour. The organic layer was separated, washed with water, dried over Na$_2$SO$_4$, filtered through silica and the filtrate mixed with equal volume of hexane and distilled to remove most of the methylene chloride and cooled to yield 30.5 g of diethyl 5-(1-methyl-5-methylthio-2-pyrroyl)-1,2-dihydro-6-methyl-3H-pyrrolo-[1,2-a]pyrrole-1,7-dicarboxylate as white crystals, m.p. 142°–3° C.

Step I: Preparation of 5-(1-methyl-5-methylthio-2-pyrroyl)-1,2-dihydro-6-methyl-3H-pyrrolo [1,2-a]-pyrrole-1,7-dicarboxylic acid Diethyl 5-(1-methyl-5-methylthio-2-pyrroyl)-1,2-dihydro-6-methyl-3H-pyrrolo[1,2-a]pyrrole-1,7-dicarboxylate (25 g) in 200 ml methanol, 50 ml H$_2$O and 25 g KOH were heated to reflux for 8 hours. The resulting mixture was treated with 200 ml of std. NaCl and distilled to remove the methanol. The mixture was acidified with 6N HCl while stirring and then cooled. The crystalline mass obtained was separated by filtration, air dried and recrystallized from ethylacetate-ethanol to yield 21 g of 5-(1-methyl-5-methylthio-2-pyrroyl)-1,2-dihydro-6-methyl-3H-pyrrolo-[1,2-a]pyrrole-1,7-dicarboxylic acid, m.p. 212°–3° C.

Step J: Preparation of ethyl 5-(1-methyl-5-methylthio-2-pyrroyl)-1,2-dihydro-6-methyl-3H-pyrrolo-[1,2-a]pyrrole-1-carboxylate-7-carboxylic acid A solution of 5-(1-methyl-5-methylthio-2-pyrroyl)-1,2-dihydro-6-methyl-3H-pyrrolo[1,2-a]pyrrole-1,7-dicarboxylic acid (20 g) and 20 g of resin (Biorad AG 50W-XB, 20–50 mesh) in 500 ml of abs. ethanol was heated to reflux until the reaction was complete by TLC (6hrs). The solution was filtered hot and the crystalline product formed was recovered by a second filtration to yield 17.5 g of ethyl 5-(1-methyl-5-methylthio-2-pyrroyl)-1,2-dihydro-6-methyl-3H-pyrrolo-[1,2-a]-pyrrole-1-carboxylate-7-carboxylic acid, m.p. 209°–211° C.

Step K: Preparation of ethyl 5-(1-methyl-5-methylthio-2-pyrroyl)-1,2-dihydro-6-methyl-3H-pyrrolo-[1,2-a]pyrrole-1-carboxylate Ethyl 5-(1-methyl-5-methylthio-2-pyrroyl)-1,2-dihydro-6-methyl-3H-pyrrolo[1,2-a]pyrrole-1-carboxylate-7-carboxylic acid (1.65 g neat) was heated at 240° C. until bubbling of CO$_2$ stops (30 minutes). The resulting residue was then dissolved in 30 ml of methylene chloride and passed through a short column of silica. The filtrate was mixed with an equal volume of hexane and then distilled to its initial volume. Cooling gave 1.1 g of ethyl 5-(1-methyl-5-methylthio-2-pyrroyl)-1,2-dihydro-6-methyl-3H-pyrrolo-[1,2-a]pyrrole-1-carboxylate as white crystals, m.p. 101°–2° C.

Following substantially the same procedure but using 5-(1-methyl-5-methylthio-2-pyrroyl)-1,2-dihydro-6-methyl-3H-pyrrolo[1,2-a]pyrrole-1,7-dicarboxylic acid as the starting material, there was obtained 5-(5-methylthio-2-pyrroyl)-1,2-dihydro-6-methyl-3H-pyrrolo[1,2-a]pyrrole-1-carboxylic acid.

EXAMPLE 2

5-(1-methyl-5-methylthio-2-pyrroyl)-1,2-dihydro-6-methyl-3H-pyrrolo-[1,2-a]pyrrole-1-carboxylic acid Ethyl 5-(1-methyl-5-methylthio-2-pyrroyl)-1,2-dihydro-6-methyl-3H-pyrrolo[1,2-a]pyrrole-1-carboxylate (500 mg) was stirred with 10 ml of methanol and 10 ml of 10% NaOH for two hours. 200 ml of saturated sodium chloride solution was added to the resulting mixture and the methanol distilled off under reduced pressure. The aqueous solution was acidified with 3N HCl while stirring, cooled and the resulting precipitate collected by filtration. The residue was washed with water, air dried and recrystallized from ethylacetate-hexane to yield 450 mg of 5-(1-methyl-5-methylthio-2-pyrroyl)-1,2-dihydro-6-methyl-3H-pyrrolo[1,2-a]pyrrole-1-carboxylic acid, m.p. 182°–184° C.

Alternatively, the title compound is prepared by decarboxylating of the corresponding diacid 5-(1-methyl-5-methylthio-2-pyrroyl)-1,2-dihydro-6-methyl-3H-pyrrolo[1,2-a]pyrrole-1,7-dicarboxylic acid in trifluoroacetic acid at about 30°–40° C. until the reaction is substantially complete. The mixture was quenched with water, extracted with methylene chloride and the methylene chloride layer was washed several times with 5% aqueous NaHCO$_3$ solution, dried and evaporated to yield 5-(1-methyl-5-methylthio-2-pyrroyl)-1,2-dihydro-6-methyl-3H-pyrrolo-[1,2-a]pyrrole-1-carboxylic acid.

EXAMPLE 3

Ethyl-5-(1-methyl-5-chloro-2-pyrroyl)-1,2-dihydro-6-methyl-3H-pyrrole[1,2-a]pyrrole-1-carboxyate Step A: Preparation of diethyl 5-(1-methyl-5-chloro-2-pyrroyl)-1,2-dihydro-6-methyl-3H-pyrrolo-[1,2a]pyrrole-1,7-dicarboxylate A solution of 16 g of diethyl 1,2-dihyro-3H-pyrrole[1,2a]-6-methylpyrrole-1,7-dicarboxylate-5-acid chloride and 6 g of 1-methyl-5-chloropyrrole in 100 ml methylene chloride was treated with 15 ml SnCl$_4$ at −35° C. and stirred at room temperature for 4 hours and worked up as described in Example 1, Step H to yield 14 g of crude product consisting of two compounds (α and β isomers). The α isomer was separated by column chromatography using silica gel as the solid support and 40:60 (ethyl acetate:hexane) as the mobile phase. The diester was crystallized from methylene chloride-hexane to yield 6.9 g of diethyl 5-(1-methyl-5-chloro-2-pyrroyl)-1,2-dihydro-6-methyl-3H-pyrrole-[1,2a]pyrrole-1,7-dicarboxylate, m.p. 124°–6° C.

Step B: Preparation of 5-(1-methyl-5-chloro-2-pyrroyl)-1,2-dihydro-6-methyl-3H-pyrrole-[1,2a]pyrrole-1,7-dicarboxylic acid 6.0 g of the diester was hydrolyzed as in Example 1, Step I and 5.2 g of 5-(1-methyl-5-chloro-2-pyrroyl)-1,2-dihydro-6-methyl-3H-pyrrole-[1,2-a]pyrrole-1,7-dicarboxylic acid was obtained.

Step C: Preparation of ethyl 5-(1-methyl-5-chloro-2-pyrroyl)-1,2-dihydro-6-methyl-3H-pyrrole-[1,2-a]pyrrole-1-carboxylate-7-carboxylic acid A solution of 5 g 5-(1-methyl-5-chloro-2-pyrroyl)-1,2-dihydro-6-methyl-3H-pyrrolo-[1,2-a]pyrrole-1,7,dicarboxylic acid in 100 ml of ethanol was treated with 5 g of resin and was monoesterified as in Example 1, Step J, to yield 3.8 g of ethyl 5-(1-methyl-5-chloro-2-pyrroyl)-1,2-dihydro-6-methyl-3H-pyrrole-[1,2-a]pyrrole-1-carboxylate-7-carboxylic acid, m.p. 185°–187° C.

Step D: Preparation of ethyl 5-(1-methyl-5-chloro-2-pyrroyl)-1,2-dihydro-6-methyl-3H-pyrrole[1,2,-a]pyrrole-1-carboxylate Following substantially the same procedure as described in Example 1, Step K, ethyl 5-(1-methyl-5-chloro-2-pyrroyl)-1,2-dihydro-6-methyl-3H-pyrrolo-[1,2-a]pyrrole-1-carboxylate-7-carboxylic acid (3.5 g) was decarboxylated at 200° C. to afford 2.5 g of ethyl 5-(1-methyl-5-chloro-2-pyrroyl)-1,2-dihydro-6-methyl-3H-pyrrole[1,2-a]pyrrole-1-carboxylate.

EXAMPLE 4

N-acetylaminoethyl 5-(1-methyl-5-chloro-2-pyrroyl)-1,2-dihydro-6-methyl-3H-pyrrole-[1,2-a]pyrrole-1-carboxylate A solution of 0.5 g of 5-(1-methyl-5-chloro-2-pyrroyl)-1,2-dihydro-6-methyl-3H-pyrrole[1,2-a]pyrrole-1-carboxylic acid 0.26 g N-acetylaminoethanol, 0.5 g DCC and 0.11 g of N,N-dimethylaminopyridine in 35 ml of methylene chloride was stirred at room temperature for 16 hours. The dicyclohexyl urea formed was filtered off and the residue dissolved in ether washed with water, 3×50 ml 5% acetic acid, 5% NaHCO$_3$, dried and evaporated. Crystallization from ethylacetate gave 401 mg of N-acetylaminoethyl 5-(1-methyl-5-chloro-2-pyrroyl)-1,2-dihydro-6-methyl-3H-pyrrolo-[1,2-a]pyrrole-1-carboxylate, m.p. 156°–157° C.

EXAMPLE 5

Lysine salt of 5-(1-methyl-5-methylthio-2-pyrroyl)-1,2-dihydro-6-methyl-3H-pyrrole-[1,2-a]pyrrole-1-carboxylic acid A solution of 0.5 g of 5-(1-methyl-5-methylthio-2-pyrroyl)-1,2-dihydro-6-methyl-3H-pyrrole-[1,2-a]pyrrole-1-carboxylic acid and 0.24 g lysine in 20 ml of methanol was stirred at 40° C. for 1 hour and then cooled and ether added slowly. The resulting precipitate was collected by filtration to afford 0.70 g of the Lysine salt.

Mass under m/e (M$^+$-H$_2$O), 446.

EXAMPLE 6

5-(1-methyl-5-methylsulfinyl-2-pyrroyl)-1,2-dihydro-6-methyl-3H-pyrrole-[1,2-a]pyrrole-1-carboxylic acid A solution of 0.2 g of 5-(1-methyl-5-methylthio-2-pyrroyl)-1,2-dihydro-6-methyl-3H-pyrrolo-[1,2-a]-pyrrole-1-carboxylic acid in 20 ml chloroform and a few drops of dimethylsulfoxide was treated with 0.1 g of m-chloroperbenzoic acid (MCPBA) and stirred overnight. Hexane was then added carefully, and the mixture was cooled and the resulting yellow crystals was collected by filtration to give 195 mg of 5-(1-methyl-5-methylsulfinyl-2-pyrroyl)-1,2-dihydro-6-methyl-3H-pyrrolo-[1,2-a]pyrrole-1-carboxylic acid. m/e 334.

Similarly the corresponding sulfone is prepared by a similar procedure using 0.2 g of (MCPBA). After refluxing overnight, there is obtained 5-(1-methyl-5-methylsulfonyl-2-pyrroyl)-1,2-dihydro-6-methyl-3H-pyrrolo- [1,2-a]pyrrole-1-carboxylic acid.

The novel compounds of this invention are anti-inflammatory, and analgesic agents of value in the treatment of a wide variety of conditions where one or more of the symptoms of pain or inflammation are manifested, e.g., rheumatoid arthritis, osteoarthritis, gout, infectious arthritis, rheumatic fever and pain symptoms associated with other diseases. Furthermore, at similar dosage levels, they are found to be unexpectedly more effective than the prior art compound (U.S. Pat. No. 3,952,012), but exhibit a much lower incidence of undesirable gastric side effects. These observations are substantiated by side-by-side comparative data as shown below in Table IV.

| Compound | (THLF(UD$_{50}$))[a] mg/kg | PBQ[b](ED$_{50}$) mg/kg | Adjuvant (ED$_{50}$)[c] mg/kg |
|---|---|---|---|
| Prior Art Compound | | | |
| RZ = H R$^4$ = C$_2$H$_5$ | 10 | 1 | 30 No protection from bone and cartilage destruction at 30 mg/kg |
| RZ = CH$_3$S R$^4$ = H | 15 | — | — |
| RZ = CH$_3$S R$^4$ = C$_2$H$_5$ | 90 | 0.17 | 7.5 Protection from bone and cartilage destruction at 10 mg/kg |
| RZ = Cl R$^4$ = H | 15 | 2.1 | — | a. Gastric Hemorrhage:

The GHLF test is conducted according to the following procedure:

Rats (Sprague-Dawley, Males, 120–180 gm) were fasted overnight and dosed orally with drug suspended in 0.5% methylcellulose. The drug concentration was adjusted so that each animal received 1.0 ml/100 gm body weight. Four hours later the animals were killed by asphixiation in carbon dioxide, the stomachs removed, cut open and everted. The mucosal lining was washed and examined under 3X magnification. The lesions are indentified as perforations of the gastric mucosa many of which perforate right through the wall of the stomach.

The results are expressed in two ways, the average number of lesions per stomach, and the number of animals in the group showing at least one lesion.

b. Inhibition of phenylbenzquinone (PBQ) writhing in mice:

Groups of 10 male mice (C.B.L., $CD_1$, 18–22 grams) were food deprived overnight prior to the experiments. Test substances, suspended or dissolved in 1% methylcellulose, were administered orally (0.1 ml/10 grams body weight) at various times prior to administration of PBQ (2.0 mg/kg i.p.). The mice were placed in individual boxes and observed for 10 minutes (5 to 15 minutes after PBQ). The number of "writhes" (abdominal contraction, lordosis and hindlimb extension) for each animal was recorded and the group means and standard errors were calculated. The means obtained from drug treated groups were compared with the vehicle control mean values and percent inhibition of writhing was calculated as follows:

$$\% \text{ Inhibition} = 100 - \left[ \frac{\text{drug group mean}}{\text{control group mean}} \times 100 \right]$$

c. Rat adjuvant arthritis test (adjuvant)

The test was done in accordance with procedures well-known in the art (see: C. A. Winter, Arthr. Rheum 9, 394–404 (1966).

For treatment of inflammation, fever or pain, the compounds of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional escipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

Dosage levels of the order to 0.2 mg to 140 mg per kilogram of body weight per day are useful in the treatment of the above-indicated conditions (10 mg to 7 gms. per patient per day). For example, inflammation is effectively treated and anti-pyretic and analgesic activity manifested by the administration from about 0.5 to 50 mg of the compound per kilogram of body weight per day (25 mg to 3.5 gms per patient per day). Advantageously, from about 2 mg to about 20 mg per kilogram of body weight per daily dosage produces highly effective results (50 mg to 1 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compound with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

What is claimed is:

1. A compound of the structural formula:

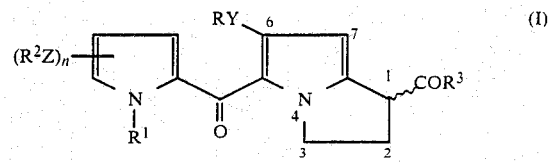

or a pharmaceutically acceptable salt thereof wherein
R is
 (a) hydrogen;
 (b) loweralkyl;
 (c) lowercycloalkyl;
 (d) lower(cycloalkyl-alkyl);
 (e) loweralkenyl;
 (f) halo-loweralkyl; or
 (g) phenyl- or phenyl-loweralkyl;
$R^1$ is hydrogen; loweralkyl; or lower haloalkyl;
$R^2Z$ can be at any available positions and $R^2$ is R as previously defined;
n is 1 to 3;
$R^3$ is
 (a) hydroxy;
 (b) loweralkoxy;
 (c) amino;
 (d) loweralkylamino;
 (e) di(loweralkyl)amino;
 (f) morpholinyl;
 (g) bis(hydroxyloweralkyl)amino;
 (h) loweralkylcyclohexylamino;
 (i) glucosamino;
 (j) lower(alkanoyloxyalkoxy);
 (k) aroyloxyloweralkoxy;
 (l) lower(alkoxycarbonyloxyalkoxy);
 (m) aryloxycarbonyloxyloweralkoxy;
 (n) tri(loweralkylamino)loweralkoxy;
 (o) lower(alkanoylaminoalkoxy);
 (p) imidoloweralkoxy;
 (q) hydroxyloweralkoxy;
 (r) loweralkoxyalkoxy;
 (s) di(loweralkylamino)loweralkoxy;
 (t) N-pyrrolidinylloweralkoxy;
 (u) N-piperidinylloweralkoxy;
 (v) N-morpholinylloweralkoxy; or
 (w) 4-methyl-1-piperazinylloweralkoxy
Y is $CH_2$ or H with the proviso that when Y is H, R is not present;
Z is —O—, a sulfur-containing group selected from a group of —S—, —SO— and —SO$_2$—, —NH— or halo providing that when Z is halo, R is not present.

2. The compound of claim 1 wherein
R is
 (a) H or $C_{1-6}$ alkyl;
 (b) $C_{2-4}$ alkenyl;
 (c) halo—$C_{1-6}$ alkyl; or
 (d) phenyl—$C_{1-3}$ alkyl;
$R^1$ is hydrogen or $C_{1-6}$ alkyl;
$R^2Z$ is at position 5 and $R^2$ is R as defined above;
n is 1;
$R^3$ is hydroxy, $C_{1-6}$ alkoxy or lower(alkanoylaminoalkoxy);
Y is oxygen, sulfur, $CH_2$— or H with the proviso that when Y is H, R is absent; and
Z is —S—, —$CH_2$— or halo with the proviso that when Z is halo, $R^2$ is absent.

3. The compound of claim 1 wherein
$R_1$ is $C_{1-3}$ alkyl or absent;

$R^1$ is hydrogen or methyl;

$R^2Z$ is at position 5 and $R^2$ is R as defined above;

n is 1;

$R^3$ is hydroxy, $C_{1-6}$ alkoxy or acetamidoethoxy;

Y is oxygen, $CH_2$— or H with the proviso that when Y is H, $R^2$ is absent; and Z is —S—, —$CH_2$—, or halo with the proviso that when Z is halo, $R^2$ is absent.

4. The compound of claim 1 which is:
  (1) 5-(5-methylthio-2-pyrroyl)-1,2-dihydro-6-methyl-3H-pyrrolo[1,2-a]pyrrole-1-carboxylic acid;
  (2) ethyl 5-(5-methylthio-2-pyrroyl)-1,2-dihydro-6-methyl-3H-pyrrolo[1,2-a]pyrrole-1-carboxylate; or
  (3) 5-(1-methyl-5-methylthio-2-pyrroyl)-1,2-dihydro-6-methyl-3H-pyrrolo[1,2-a]pyrrole-1-carboxylic acid;
  (4) ethyl 5-(1-methyl-5-methylthio-2-pyrroyl-1,2-dihydro-6-methyl-3H-pyrrolo[1,2-a]pyrrole-1-carboxylate;
  (5) 5-(1-methyl-5-ethylthio-2-pyrroyl)-1,2-dihydro-6-methyl-3H-pyrrolo[1,2-a]pyrrole-1-carboxylic acid;
  (6) 5-(1-methyl-5-n-propylthio-2-pyrroyl)-1,2-dihydro-6-methyl-3H-pyrrolo[1,2-a]pyrrole-1-carboxylic acid;
  (7) 5-(1-trifluoromethyl-5-methylthio-2-pyrroyl)-1,2-dihydro-6-methyl-3H-pyrrolo[1,2-a]pyrrole-1-carboxylic acid;
  (8) ethyl-5-(1-methyl-5ethylthio-2-pyrroyl)-1,2-dihydro-6-methyl-3H-pyrrolo[1,2-a]pyrrole-1-carboxylate;
  (9) ethyl 5-(1-methyl-5-n-propylthio-2-pyrroyl)-1,2-dihydro-6-methyl-3H-pyrrolo[1,2-a]pyrrole-1-carboxylate;
  (10) ethyl 5-(1-trifluoromethyl-5-methylthio-2-pyrroyl)-1,2-dihydro-6-methyl-3H-pyrrolo[1,2-a]pyrrole-1-carboxylate; or a lysine salt thereof.

5. The compound of claim 4 which is
(a) l-isomer;
(b) d-isomer; or
(c) a mixture of l-and d-isomers.

6. The compound of claim 1 which is
  (1) 5-(5-chloro-2-pyrroyl)-1,2-dihydro-6-methyl-3H-pyrrolo[1,2-a]pyrrole-1-carboxylic acid;
  (2) ethyl 5-(5-chloro-2-pyrroyl)-1,2-dihydro-6-methyl-3H-pyrrolo[1,2-a]pyrrole-1-carboxylate;
  (3) 5-(1-methyl-5-chloro-2-pyrroyl)-1,2-dihydro-6-methyl-3H-pyrrolo[1,2-a]pyrrole-1-carboxylic acid; or
  (4) ethyl 5-(1-methyl-5-chloro-2-pyrroyl)-1,2-dihydro-6-methyl-3H-pyrrolo[1,2-a]pyrrole-1-carboxylate.

7. The compound of claim 1 which is:
  (1) 5-(5-isopropyl-2-pyrroyl)-1,2-dihydro-6-methyl-3H-pyrrolo[1,2-a]pyrrole-1-carboxylic acid;
  (2) ethyl 5-(5-isopropyl-2-pyrroyl)-1,2-dihydro-6-methyl-3H-pyrrolo[1,2-a]pyrrole-1-carboxylate;
  (3) 5-(1-methyl-5-isopropyl-2-pyrroyl)-1,2-dihydro-6-methyl-3H-pyrrolo[1,2-a]pyrrole-1-carboxylic acid; or
  (4) ethyl 5-(1-methyl-5-isopropyl-2-pyrroyl)-1,2-dighydro-6-methyl-3H-pyrrolo[1,2-a]pyrrole-1-carboxylate.

8. The compound of claim 1 which is
  (1) 5-(1-methyl-5-methoxy-2-pyrroyl)-1,2-dihydro-6-methyl-3H-pyrrolo[1,2-a]pyrrole-1-carboxylic acid;
  (2) 5-(1-methyl-5-ethoxy-2-pyrroyl)-1,2-dihydro-6-methyl-3H-pyrrolo [1,2-a]pyrrole-1-carboxylic acid;
  (3) 5-(1-methyl-5-n-propyloxy-2-pyrroyl)-1,2-dihydro-6-methyl-3H-pyrrolo[1,2-a]pyrrole-1-carboxylic acid;
  (4) ethyl 5-(1-methyl-5-methoxy-2-pyrroyl)-1,2-dihydro-6-methyl-3H-pyrrolo[1,2-a]pyrrole-1-carboxylate;
  (5) ethyl 5-(1-methyl-5-ethoxy-2-pyrroyl)-1,2-dihydro-6-methyl-3H-pyrrolo[1,2-a]pyrrole-1-carboxylate; or
  (6) ethyl 5-(1-methyl-5-n-propyloxy-2-pyrroyl)-1,2-dihydro-6-methyl-3H-pyrrolo[1,2-a]pyrrole-1-carboxylate.

* * * * *